United States Patent [19]

Smith et al.

[11] 3,993,700

[45] Nov. 23, 1976

[54] PURIFICATION OF P-PHENYLPHENOL

[75] Inventors: William E. Smith; Irvin W. Potts, Jr., both of Midland, Mich.

[73] Assignee: The Dow Chemical Company, Midland, Mich.

[22] Filed: Feb. 20, 1973

[21] Appl. No.: 333,863

[52] U.S. Cl. .............................................. 260/620
[51] Int. Cl.² ........................................ C07C 37/44
[58] Field of Search .................................... 260/620

[56] References Cited
UNITED STATES PATENTS

| | | | |
|---|---|---|---|
| 1,996,744 | 4/1935 | Britton | 260/620 |
| 2,129,908 | 9/1938 | Britton | 260/620 |

*Primary Examiner*—Norman Morgenstern
*Attorney, Agent, or Firm*—Ralph M. Mellom

[57] ABSTRACT

A purified p-phenylphenol is obtained by reduction of the m-phenylphenol percentage from crude or technical grade p-phenylphenol by contacting the mixture with a molar quantity of caustic less than heretofore employed, whereby the m-phenylphenol preferentially reacts to form sodium m-phenylphenate while the p-phenylphenol ends up as a solid in substantially pure form. The amount of the caustic is from about 0.5 to about 10 moles of caustic per mole of m-phenylphenol present. Resin grade p-phenylphenol, i.e., containing less than 2% m-phenylphenol can be obtained from a starting material containing up to 30% m-phenylphenol.

11 Claims, No Drawings

PURIFICATION OF P-PHENYLPHENOL

BACKGROUND OF THE INVENTION

Separation of m-phenylphenol and p-phenylphenol has posed a serious problem in preparing resin grade p-phenylphenol. Separation of o-phenylphenol from these two isomers is normally accomplished by distillation, but the m- and p-isomers cannot be separated in this manner because of the close boiling points.

In the past, these two isomers have been separated by two methods. The first method is described in U.S. Pat. No. 2,129,908 whereby m-phenylphenol is separated from a mixture of m- and p-phenylphenols either by leaching out the meta compound from the mixture with an organic solvent at a temperature at which the para compound is substantially insoluble therein or by dissolving the aforesaid phenylphenol mixture in a heated organic solvent and then cooling the solution to precipitate the para compound. The patent goes on to say that the p-phenylphenol is thus partially purified (containing about 5% of m-phenylphenol) and that this can be further purified by using hot caustic to dissolve all of the phenylphenol. The hot solution is then cooled whereby crystallization of the sodium p-phenylphenate occurs.

A second method used in industry borrows in part from the above. That is to say, technical grade or crude p-phenylphenol containing an undesirable amount of m-phenylphenol is entirely dissolved in excess caustic. This reaction produces sodium m-phenylphenate and sodium p-phenylphenate, the cooled solution producing crystallization of the sodium p-phenylphenate. These crystals are then filtered off, washed with cold water and redissolved in boiling water. Resultant solution is then acidified with dilute sulfuric acid whereby p-phenylphenol is precipitated. The disadvantage of this process is that there are two waste streams that have to be sent to waste disposal.

Due to the great expense of these techniques, research has been conducted to solve this problem. The present invention is a result of such research.

SUMMARY OF THE INVENTION

It has now been discovered in the present invention that a mixture of p-phenylphenol and m-phenylphenol, wherein the m-phenylphenol constitutes about 30% or less by weight of the mixture, can be separated to produce a p-phenylphenol of resin grade quality, i.e., one that contains about 2% or less of m-phenylphenol. The novel process of the subject invention eliminates two undesirable waste streams as well as two steps of the old process. In the old process, molten crude or technical grade p-phenylphenol was fed into a reactor along with concentrated caustic which was supplied in molar excess to the total amount of phenylphenols. Sodium p-phenylphenate was then crystallized out and fed into a filter where it was washed with water, creating a waste stream at that point. The washed sodium p-phenylphenate was then fed into a neutralizer and converted into p-phenylphenol by the reaction of dilute sulfuric acid. The resulting p-phenylphenol was then fed into a filter and collected while being washed again with water creating a second waste disposal stream.

Under the new process of this invention, crude or technical grade p-phenylphenol, containing about 30% or less of m-phenylphenol is reacted with at least about 50% less caustic than used in the old process. The reactions that take place selectively convert the m-phenylphenol to sodium m-phenylphenate, leaving the bulk of the p-phenylphenol unreacted. The p-phenylphenol is then sent to a filter where it is washed. The stream from the filter can then be utilized to make other products such as mixed m- and p-biphenylylphenyl ethers and the like. Where necessary and where desired, i.e., where the p-phenylphenol still contains more than about 2% of m-phenylphenol and that is the ultimate goal, these process steps are easily repeated by recycling this mixture for repeated leachings by the caustic. The need to recycle will depend on the amount of m-phenylphenol present in the crude or technical grade p-phenylphenol at the outset. Thus, where the crude or technical grade p-phenylphenol is the product of a chlorobenzene hydrolysis of phenol, the percentage by weight of m-phenylphenol in the mixture will be from about 3 to about 5% by weight. In such case, one leaching will be all that is necessary. Where the phenylphenol mixture is obtained as a by-product from the hydrolysis of halogenated diphenyl, the m-phenylphenol present in the mixture may be as high as 30%. In such cases, the leaching contemplated by this invention can be repeated until the amount of m-phenylphenol reaches acceptable limits. Where the crude or technical grade p-phenylphenol is the result of combining streams from the phenol and diphenyl process, recycling of the p-phenylphenol may again be employed, depending on whether resin grade is desired or just a p-phenylphenol having a lower percentage of the m-isomer for some other use.

The fact that the m-phenylphenol can be "extracted" from the crude or technical grade p-phenylphenol mixture by using lower molar amounts of caustic to selectively convert the m-isomer to the water-soluble salt while leaving the p-phenylphenol comparatively unreacted in a mixture of the two where the m-phenylphenol represents only a minor portion thereof, is a unique phenomenon.

Examination of the chemistry surrounding this new technique would not lead one to believe that the m-phenylphenol would be preferentially removed. One would expect the caustic to react with the p-phenylphenol in preference to the m-phenylphenol owing to the law of mass action (from about 70 to about 97 parts of p-phenylphenol being present to from about 30 to about 3 parts of m-phenylphenol). Accordingly, one would expect that the main reaction would be to produce sodium p-phenylphenate to the exclusion of any substantial amount of sodium m-phenylphenate. As will be shown below, this is not what happens.

Nor is the m-phenylphenol reacted selectively because it is a stronger acid. In fact, although the pKa values of the two isomers are very close, p-phenylphenol is still the more acidic. m-Phenylphenol is reported to have a pKa of 9.6 while p-phenylphenol has a pKa value of 9.5.

The selective phenomenon which occurs is believed to be based on certain solubility differences and the following hypotheses are offered although it is to be understood that these hypotheses are being offered as such only and are not claimed herein. When the phenylphenols involved are added in molten or powdered form to the caustic solution, a fine dispersion of solid particles is produced. It is presumed that by the law of mass action, the p-phenylphenol reacts with the bulk of the caustic to give sodium p-phenylphenate. The prior art and past experience shows that sodium p-phenylphenate is not as soluble in water as sodium m-phenylphenate. Assuming that an equilibrium reaction exists between sodium p-phenylphenate and m-phenylphenol to give p-phenylphenol and sodium m-phenylphenate, a possible explanation for the desired separation of the two isomers is as follows. The sodium m-phenylphenate being more soluble is removed thus driving the equilibrium in favor of the formation of more sodium m-phenylphenate. This hypothesis can be depicted as follows:

caustic and the m-phenylphenol. In the preferred technique, after the o-phenylphenol is distilled leaving the crude p-phenylphenol and m-phenylphenol mixture, the latter mixture is distilled to remove the tars and the molten technical grade p-phenylphenol is then extracted in dilute caustic, filtered and leached in dilute caustic, separated from the water phase and dried in a pressure decanter and finally the purified p-phenylphenol is distilled to remove the final tars.

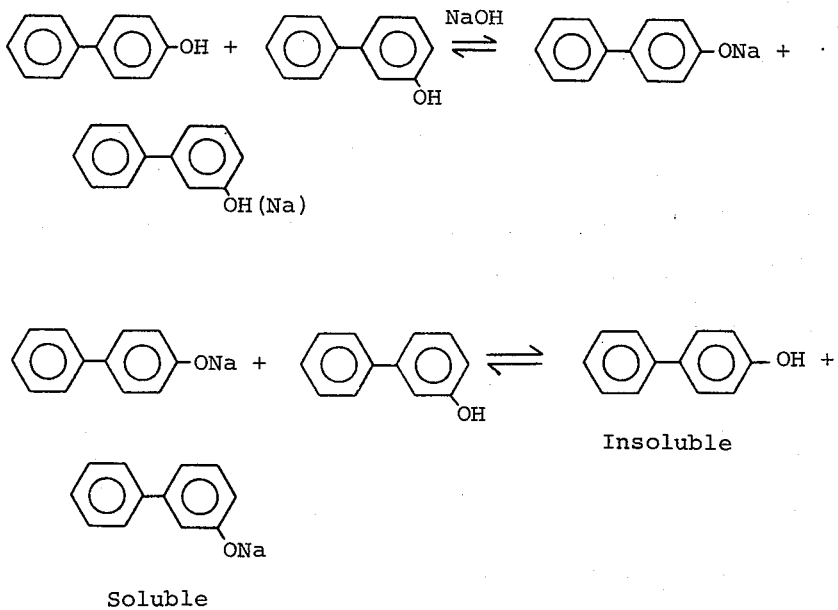

The purification method of the invention can be used to separate any mixture of p-phenylphenols and m-phenylphenols wherein the p-phenylphenol component is the major component. Preferred separations, however, are carried out on mixtures that contain 30% m-phenylphenol or less. Such mixtures may contain in addition to the p- and m-phenylphenols other components which do not deleteriously affect the separation, including o-phenylphenol and tars containing complex polyphenyls.

The techniques used to purify the crude or technical grade p-phenylphenol involve contacting the aqueous caustic solution with the phenylphenol mixture under conditions which allow the caustic to react selectively with the m-phenylphenol but only a small fraction of the p-phenylphenol. The contact is conveniently accomplished by adding the phenylphenol mixture in molten or powder form into the caustic accompanied by mixing, by washing a solid phenylphenol mixture with the aqueous caustic solution using techniques such as counter-current leaching, cyclic leaching and the like. Using these techniques or any other technique contacting the mixtures wherein mixing occurs, m-phenylphenol is readily reacted in the aqueous caustic to form a soluble sodium m-phenylphenate leaving a purified p-phenylphenol in solid form.

The process of the invention, as indicated, is employable with a crude p-phenylphenol or technical grade p-phenylphenol as the starting material. The sole difference between crude p-phenylphenol and technical grade p-phenylphenol is that the crude material contains a considerable amount of tar. This presence of tar poses no problem with regard to the reaction of the Another equally good method would be to carry out the reaction in a counter-current solids leaching apparatus on a continuous basis. This process would involve three unit operations at most: extraction, drying and distillation.

The temperature conditions at which the phenylphenol mixture and the caustic are contacted can vary between 0° and about 150° C. Preferred temperature conditions during the reaction of the caustic with the phenylphenol mixture are from about 50° to about 100° C. Thus, preferentially, the caustic solution can be boiling or as low as about 30° at the time of contact. The ensuing exothermic reaction will raise the temperature to from about 50° to about 100° C. and after reaction, can be cooled for the filtration step.

The ratio of water to crude or technical grade p-phenylphenol is of little consequence; however, at a ratio of less than 2 parts water to 1 part feed, working with the slurry becomes increasingly difficult.

Similarly, the contact time can vary widely between about 1 minute and about 15 hours. Preferably, it is between about 10 minutes to about 3 hours. This will be dependent somewhat on the temperatures used, the ratio of the caustic to the m-phenylphenol, which in turn is dependent on the percent by weight of the m-phenylphenol in the mixture of phenylphenols.

The crux of the invention resides in the ratio of the caustic to the m-phenylphenol present in the mixture. As shown in the prior art, if the mole ratio of the caustic to the total phenylphenols in the mixture is 1:1 or greater than 1:1, all of the phenylphenols will be reacted to form the sodium salt.

When the percentage of the m-phenylphenol in the crude or technical grade p-phenylphenol is high, i.e., 12 to 30%, the efficiency of the process of the invention increases with a decrease in the ratio of the caustic to the m-phenylphenol. Conversely, when the m-phenylphenol percentage is in the lower ranges, larger ratios of caustic to m-phenylphenol can be employed with excellent results. The overall ratio can range from about 0.5 mole of caustic to 1 mole of m-phenylphenol in the starting material to from about 10 moles of caustic to 1 mole of m-phenylphenol. Thus, where the crude or technical grade p-phenylphenol initially contains from about 30 to about 12% m-isomer, the mole ratio of caustic to m-phenylphenol is preferentially from about 0.5 to 1, to about 2 to 1. As will be shown by the examples below, dramatic decreases in the m-phenylphenol percentage remaining in p-phenylphenol are obtained in these higher ranges of m-phenylphenol impurity. The filtered cake of p-phenylphenol in such cases can be further purified to any desired amount of m-phenylphenol percentage by one or more successive leachings utilizing the process of the invention. Where the m-phenylphenol impurity is less than about 12%, the mole ratio is preferably from about 2 to 1 to about 10 to 1. Where the m-phenylphenol is about 6% or less of the starting material, one leaching utilizing the process of the invention is sufficient to produce a purified p-phenylphenol of resin grade, i.e. containing less than about 2% m-phenylphenol.

SPECIFIC EMBODIMENTS

EXAMPLE 1

To a 1000 ml. round-bottomed flask fitted with a stirrer and condenser, 500 ml. of water and sodium hydroxide were added. The solution was warmed to 80°–90° C. and 100 g. of molten technical grade p-phenylphenol was added with stirring. The p-phenylphenol mixture contained 0.4% o-isomer, 3.1% m-isomer and 93.5% p-isomer. The mixture was stirred for 15 minutes and the solids collected on a filter. The cake was dried and the p-phenylphenol was distilled to give product, having the following analysis for each run.

TABLE I

| Sample* | Moles NaOH/Moles MPP | OPP | MPP | PPP |
| --- | --- | --- | --- | --- |
| Run 1 | 2.5 | 0.2 | 2.32 | 97.1 |
| Run 2 | 5.0 | <0.1 | 1.15 | 98.81 |
| Run 3 | 6.0 | <0.1 | 0.80 | 97.9 |
| Run 4 | 10.0 | <0.1 | 0.80 | 97.60 |

*Analysis of distillate

EXAMPLE 2

To a 100 ml. beaker, 25 g. of the starting phenylphenol mixture used in Example 1, above, and water containing 1.0 g. of sodium hydroxide were added. The mixture was heated to 95° C. and stirred for 10 minutes after reaching this temperature. This gave a mole ratio of caustic to m-phenylphenol of about 5.55 to 1. Water was added to maintain volume. The solid was collected on a filter. The cake was treated with small amounts of hydrochloric acid and dried. The resulting p-phenylphenol was analyzed and shown to have 1.2% of m-phenylphenol present therein.

EXAMPLE 3

50.8 g. of technical grade p-phenylphenol containing 2.8% m-phenylphenol was heated to a molten state and added to a boiling caustic solution of 0.925 g. of sodium hydroxide in 250 g. of water with stirring. The contact time was 10 minutes. This gave a mole ratio of caustic to m-isomer of 2.58 to 1. The raffinate weighed 40.4 g. and comprised 1.2% m-isomer and 94.7% p-isomer which gave a recovery of p-phenylphenol of 82%. The filtrate weighed 4.0 g. (dry weight), and comprised 13.2% m-isomer and 28.8% p-isomer.

EXAMPLE 4

Using the same procedure as in Example 3, above, 100.5 g. of technical grade p-phenylphenol containing 2.0% o-isomer, 2.9% m-isomer and 87.8% p-isomer was stirred into a caustic solution of 1.867 g. sodium hydroxide in 250 g. of water, giving a mole ratio of caustic to m-isomer of 2.63. The raffinate weighed 91.7 g. and comprised 0.2% o-isomer, 1.0% m-isomer and 93.3% p-isomer, giving a recovery of 96% p-phenylphenol in the cake. The filtrate weighed 8.2 g. and comprised 4.8% o-isomer, 13.4% m-isomer and 22.9% p-isomer.

EXAMPLE 5

137.4 g. of the technical grade p-phenylphenol feed used in Example 4, above, was stirred into a caustic mixture comprising 2.661 g. of sodium hydroxide in 500 g. of water. The conditions and procedure was the same as used in Examples 3 and 4. The mole ratio of the sodium hydroxide to the m-isomer was 2.74 to 1. Upon cooling the solution and collecting the filter cake, this raffinate weighed 117.1 g. and comprised 0.3% o-isomer, 1.2% m-isomer and 101.0% p-isomer. This amounted to a recovery of p-phenylphenol of 98%. The dry weight of the filtrate was 10.8 g. and comprised 3.9% o-isomer, 14.3% m-isomer and 48.7% p-isomer.

EXAMPLE 6

125.6 g. of technical grade p-phenylphenol feed of the same isomer percentages used in Examples 4 and 5, above, was heated to its molten state and stirred into a caustic solution containing 0.780 g. of sodium hydroxide in 200 g. of water. At the time of contact, the temperature of the caustic was 60° C. This gave a mole ratio of sodium hydroxide to m-isomer of 0.88 to 1. The raffinate comprised 0.2% o-isomer, 1.7% m-isomer and 97.1% p-isomer. This raffinate was leached again at 35° C. using a caustic solution comprising 2.0 g. of sodium hydroxide in 200 g. of water. The raffinate was recovered and again leached at 35° C. in the caustic solution comprising 2.0 g. of sodium hydroxide in 200 g. of water. This final raffinate weighed 92.1 g. and comprised 0.1% o-isomer, 1.0% m-isomer and 99.1% p-isomer for a recovery of 84% p-phenylphenol.

EXAMPLE 7

Again using the same technical grade p-phenylphenol feed used in Example 6, above, 101.3 g. of this feed in the molten state was contacted and stirred into a boiling caustic solution comprising 1.41 g. of sodium hydroxide in 227 g. of water. This gave a mole ratio of sodium hydroxide to the m-isomer of 1.96 to 1. In this case, the contact time was extended to 3 hours. The dried raffinate weighed 90.3 g. and comprised 0.5% o-isomer, 1.0% m-isomer and 94.0% p-phenylphenol which gave a recovery rate of 95% p-phenylphenol. The filtrate dry weight was only 2.8 g. and comprised 0.4% o-isomer, 10.7% m-isomer and 83.0% p-isomer.

In Examples 8 and 9, below, crude p-phenylphenol feed was employed, i.e., containing the undistilled tars. This crude feed comprised, inter alia, 0.8% o-isomer, 2.0% m-isomer and 57.8% p-isomer. Procedures employed were identical to that of Example 3, that is, the molten feed was fed into the boiling caustic with a contact time of 10 minutes with stirring.

EXAMPLE 8

150.7 g. of the crude feed was stirred into a caustic solution comprising 2.928 g. of sodium hydroxide in 750 g. of water. The raffinate weighed 21.4 g. and comprised 0.3% of o-isomer, 0.9% of m-isomer and 57.1% of the p-isomer. This gave a recovery of p-phenylphenol of 91%.

EXAMPLE 9

This example involved three leachings. The first utilized 146.9 g. of the crude feed in a caustic solution comprising 1.246 g. of sodium hydroxide in 300 g. of water. This raffinate weighing 119.5 g. was then leached at the temperature of the boiling slurry in a caustic solution comprising 0.808 g. of sodium hydroxide in 200 g. of water. The resulting raffinate was again leached at the temperature of the boiling slurry in a caustic solution comprising 0.905 g. of sodium hydroxide in 200 g. of water. This raffinate was distilled and produced a product which comprised 0.2% o-isomer, 0.4% m-isomer and 99.7% p-isomer.

EXAMPLE 10

Molten technical grade p-phenylphenol comprising 0.9% o-isomer, 3.5% m-isomer and 91.6% p-isomer was contacted with an 80° C. caustic solution wherein the sodium hydroxide to m-phenylphenol ratio was 6 to 1 and the water to total p-phenylphenols was about a 5 to 1 weight basis. Using the procedures described in Example 3, above, analysis of the p-phenylphenol cake showed 0.19% o-isomer, 1.06% m-isomer and 98.8% p-isomer.

EXAMPLE 11

Technical grade p-phenylphenol containing less than 1% o-isomer, about 30% m-isomer and about 68% of the p-phenylphenol was contacted using the process of Example 3 except that the caustic solution was at 35° C. at time of contact. The mole ratio of the sodium hydroxide to the m-isomer was about 1 to 1. The water used was at a ratio of water to the total phenylphenols at about a 5 to 1 weight basis. The filtrate analysis showed less than 0.1% o-isomer, 69.8% m-isomer and 29.7% p-isomer, while the cake analyzed out at less than 0.1 o-isomer, 18.0% m-isomer and 83.0% p-isomer.

EXAMPLE 12

Using the same feed and same caustic solution as in Example 10, above, the feed and the caustic solution were contacted at a caustic solution temperature of 55° C. Following the procedure as in Example 10, above, the filtrate was analyzed to be less than 0.1% o-isomer, 56.3% m-isomer and 36.3% p-isomer while the filtered cake analyzed out to be less than 0.1% o-isomer, 17.2% m-isomer and 73.5% p-isomer.

EXAMPLE 13

Molten technical grade p-phenylphenol containing 17.7% m-isomer was added to a caustic solution containing 1.2 moles of sodium hydroxide per 1 mole of the m-isomer. Initial caustic temperature was 50° C. The purified p-phenylphenol cake contained only 6.8% of the m-isomer while the p-phenylphenol recovery was 82%.

EXAMPLE 14

Using the same procedure as described in Example 13, above, along with the same caustic to m-isomer ratio, technical grade p-phenylphenol containing 18.2% of the m-isomer was reacted. The purified phenylphenol filter cake contained 6.3% of the m-isomer while the recovery of p-phenylphenol was 84%.

EXAMPLE 15

Using the same procedure as in Examples 13 and 14, above, along with the same caustic ratio, a technical grade p-phenylphenol containing 19.6% m-phenylphenol was reacted and gave a filter cake of p-phenylphenol containing 8.5% of the m-isomer. The p-phenylphenol recovery was 93%.

EXAMPLE 16

Molten p-phenylphenol containing 1.7% o-isomer, 4.7% m-isomer and 95.0% p-isomer was contacted with boiling caustic comprising 1.13 g. of sodium hydroxide in 222 g. of water and stirred for 10 minutes. After cooling, the resultant solids were filtered and this raffinate cake was analyzed to show 0.9% o-isomer, 1.2% m-isomer and 83.5% p-phenylphenol.

We claim:
1. The process for purifying p-phenylphenol in a mixture comprising p-phenylphenol containing about 30% or less m-phenylphenol based on the total weight of the phenylphenols, comprising (1) contacting with mixing, said mixture with an aqueous caustic solution of from about 0.5 to about 10 moles of caustic per mole of m-phenylphenol at a temperature of from about 0° C. to about 150° C. to form an aqueous phase and a solid phase, said solid phase consisting essentially of purified p-phenylphenol and (2) separating said solid phase.

2. The process of claim 1 wherein the mixture comprising p-phenylphenol contains about 12% or less m-phenylphenol based on the total weight of the phenylphenols and the aqueous caustic solution has a mole ratio of from about 2 to about 10 moles per mole of m-phenylphenol.

3. The process of claim 1 wherein the mixture comprising p-phenylphenol contains from about 30% to about 12% m-phenylphenol based on the weight of the total phenylphenols and the mole ratio of the caustic per mole of m-phenylphenol is from about 0.5 to about 2.

4. The process of claim 1 wherein the temperature is from about 50° to about 100° C.

5. The process of claim 1 wherein the separated solid p-phenylphenol contains less than about 2% by weight of m-phenylphenol.

6. The process of claim 1 wherein the mixture comprising p-phenylphenol containing about 30% or less m-phenylphenol is in the molten state when contacted with the aqueous caustic solution.

7. The process of claim 6 wherein the aqueous caustic solution at the time of contacting is at a temperature of from about 30° C. to boiling.

8. The process of claim 1 wherein the mixture comprising p-phenylphenol containing about 30% or less m-phenylphenol is in powder form when contacted with the aqueous caustic solution.

9. The process for producing resin grade p-phenylphenol from crude or technical grade p-phenylphenol containing 6% or less of m-phenylphenol based on the total weight of phenylphenols comprising (1) contacting with mixing said crude or technical grade p-phenylphenol with an aqueous caustic solution of from about 2 to about 6 moles of caustic per mole of m-phenylphenol at a temperature of from about 30° C. to about 100° C. and (2) separating the solid p-phenylphenol from the aqueous phase.

10. The process of claim 9 wherein the crude or technical grade p-phenylphenol is in the molten state when contacted with the aqueous caustic solution.

11. The process of claim 9 wherein the crude of technical grade p-phenylphenol is in powder form when contacted with the aqueous caustic solution.

* * * * *